United States Patent [19]

Bowling et al.

[11] Patent Number: 4,959,614
[45] Date of Patent: Sep. 25, 1990

[54] APPARATUS FOR DETERMINING MICROWAVE CHARACTERISTICS OF SUPERCONDUCTIVE MATERIALS USING A RESONANT CAVITY AND CALIBRATION WAVEGUIDES

[75] Inventors: Donald R. Bowling; Charles F. Smith, both of Ridgecrest, Calif.

[73] Assignee: The United States of America as Represented by the Secretary of the Navy, Washington, D.C.

[21] Appl. No.: 389,233

[22] Filed: Aug. 3, 1989

[51] Int. Cl.$^5$ .......................... G01N 22/00; H01P 7/06
[52] U.S. Cl. ...................................... 324/636; 324/71.6; 324/601; 333/99 S; 505/843
[58] Field of Search ...................... 324/71.6, 633, 636, 324/642, 691, 693, 601; 505/842, 843, 847, 845, 700, 701, 726, 727; 333/99 S

[56] References Cited

PUBLICATIONS

Chang et al., Microwave surface resistance in Tl-based superconducting thin films, 9-1989, pp. 1357-1359, 505/726.
Moffat et al., Temperature Rependence of the Surface Resistivity at 1.5 GHz and 6 GHz of single crystals, thin films and sintered pellets of YBa$_2$Cu$_3$O$_{7-x}$, 4-1988, pp. 347-350.

Primary Examiner—Reinhard J. Eisenzopf
Assistant Examiner—Jack B. Harvey
Attorney, Agent, or Firm—Sol Sheinbein; Melvin J. Sliwka; Stephen J. Church

[57] ABSTRACT

Apparatus for determining the electrical characteristics of a superconductive material in a range of microwave frequencies and in a range of cryogenic temperatures has the material incorporated within a resonant cavity mounted on a cold finger for maintaining the material at a predetermined temperature. A pair of test waveguides extend oppositely of the cavity and terminate in separable waveguide junctions for passage of microwave energy to measure the microwave characteristics of the cavity as affected by the superconductive material. The cavity and test waveguides are enclosed in a vacuum chamber from which the cold finger extends for connection to controlled temperature cryogenic cooling equipment. The chamber also contains a plurality of calibration waveguides which extend parallel to the test waveguides, each calibration waveguide terminating oppositely in separable junctions. The chamber has plates disposed oppositely of the waveguides and moveable transversely in relation to the waveguides without loss of vacuum. Each plate bears a connector waveguide having an outer portion connectable to a microwave network analyzer and having an inner portion extending through the plate and terminating in a separable junction alignable, by movement of the plate, with the junctions of the test of calibration wave guides so that the network analyzer is selectively connectable to the cavity or to a calibration waveguide without loss of vacuum or change in temperature of the superconductive material.

13 Claims, 6 Drawing Sheets

APPARATUS FOR DETERMINING MICROWAVE CHARACTERISTICS OF SUPERCONDUCTIVE MATERIALS USING A RESONANT CAVITY AND CALIBRATION WAVEGUIDES

BACKGROUND OF THE INVENTION

1. Field of the Invention

The subject invention relates to superconductive materials and wave transmission devices. More particularly, the invention relates to testing the microwave frequency impedance and transition temperature of a superconductive material by use of a resonant cavity and mechanically switched waveguides.

2. Description of the Prior Art

Superconducting materials have great potential for a variety of microwave frequency applications; however, the design of practical devices for these applications is presently severely limited by the lack of knowledge of the electrical characteristics of these materials at microwave frequencies even though the direct current characteristics may be well-known. For example, these materials, which by definition have substantially no DC resistivity, have significant losses at microwave frequencies. This lack of knowledge includes such basic information as the losses at different temperatures in a range thereof involving the transition temperature of the material to the superconducting state and the effect of varying microwave frequencies on the losses. This last effect is particularly important since the losses in a superconductor vary with the square of the frequency instead of only with the square root of the frequency as in non-superconducting metals commonly used for waveguides, antenna elements, and the like.

While the resistivity of a material at microwave frequencies is not directly measurable, there are well-known techniques fully effective at the usual environmental temperatures for deriving this resistivity from measurements of the amplitude and phase of microwave energy as affected by transmission through, reflection from, and resonance within microwave elements having an interior surface, or surface portion, of the material of interest. It is apparent that such measurements are, necessarily, carried out using waveguides and coaxial transmission lines to connect the measurement equipment, such as a well-known microwave network analyzer, to an element including such material. It is thus necessary to calibrate the measuring equipment, including any such transmission elements, by waveguides or the like of known characteristics to isolate the effects due to an element of interest from effects due to the measurement equipment itself. If the measurement equipment, transmission devices, and measured element are all at the same temperature such calibration can be effectively carried out to mathematically derive "error boxes" combining the effects of the measuring and transmission equipment. However, it is apparent that if this equipment varies in temperature, either with time or along the length of transmission elements, the temperature caused changes in length and microwave characteristics of the elements make calibration highly inaccurate if not problematical. It is also necessary that measurements be carried out shortly after calibration to minimize "drift" of the measuring equipment. It is apparent that, for meaningful calibration, any required changing of microwave connections between different calibration and test devices must occur with minimal changes in transmission element length and, to avoid changes in microwave reflection characteristics, with minimal bending of transmission elements and breaking of connections.

These difficulties in measurement and calibration are particularly serious in measurements of the microwave characteristics of superconducting materials where the measurements are necessarily carried out at cryogenic temperatures, commonly defined as below $-50°$ C., and typically involving superconductivity transition temperatures of 90° to 150° K. Insofar as known to the applicants, such measurements have hitherto been carried out by immersing a body, which defines a microwave cavity having an interior surface portion constructed of the material of interest, into liquified cryogenic gas in an open cryostat to bring such portion to the transition range, the measurements then being made with microwave connections to the body made by relatively long transmission elements extending through the liquified gas and from the body and cryostat to microwave measurement equipment at room temperature. This arrangement has a number of deficiencies.

The most serious such deficiency is due to the transmission element lengths and characteristics varying with the temperature difference along the elements so that calibration to eliminate the effects of these elements, which involves measurement of phase relations between microwave energy provided to and returned from these elements and the cavity, is not possible even if these effects were unchanging with time. It is thus not possible in the prior art arrangements to separate corresponding amplitude changes in such energy due to the superconducting material from those due to the transmission elements. A most important measurement of the characteristics of a superconductive material involves changing its temperature, as by an electric resistance heater in the cryostat and applied to the body, to determine the transition point. In such prior art arrangements this measurement itself induces time varying temperature changes in the transmission elements making it even more difficult to separate effects in the measurement equipment from those actually of interest.

Another deficiency of the prior art arrangements arises from the time required, typically 4 to 8 hours, for the transmission and cavity defining elements to cool from room temperature and stabilize sufficiently to permit even the relatively imprecise measurements hitherto possible. Measurements with these arrangements are thus very time consuming, especially when it is desired to change the cavity or superconducting element therein. This lengthy stabilization time also allows the measurement equipment to drift after calibration with elements at room temperature, further reducing the accuracy of the measurements at cryogenic temperature.

SUMMARY OF THE INVENTION

Apparatus for determining the electrical characteristics of a superconductive material in a range of microwave frequencies and over a range of cryogenic temperatures has the material incorporated in a detachable element disposed interiorly of a body which defines a resonant cavity and is detachably mounted on a cold finger of cryogenic cooling equipment for maintaining the element at a predetermined temperature. A pair of test waveguides extend oppositely from the cavity and terminate individually in separable waveguide junctions for passage of microwave energy to measure the reflection or transmission characteristics of the cavity as affected by the superconductive element. The cavity and test waveguides are enclosed in a vacuum chamber having at one side an adapter plate through which the cold finger extends from the cryogenic equipment to the cavity. The chamber has mounted therein a plurality of calibration waveguides which may be shorted or through and of different lengths. Each calibration waveguide extends parallel to the test waveguides and terminates oppositely in similar separable junctions. Preferably, the chamber is cylindrical about an axis parallel to and centrally of the waveguides and has opposite end plates rotatable about this axis in vacuum sealed relation to the balance of the chamber. Each end plate bears a connector waveguide having an outer portion connectable to a microwave network analyzer and having an inner portion extended through the end plate and terminating in a separable junction which is alignable, by pivoting the plate, with a junction of a selected one of the test or calibration wave guides. An axle extends between and pivots with the end plates for alignment of the junctions of the connector waveguides with the opposite junctions of the test waveguides or of a calibration waveguide. Each connector waveguide is, preferably, mounted in vacuum sealed, rotatable, and axially slidable relation in the corresponding plate for positioning the connector waveguide junction in mating relation with such an aligned junction.

An object of the present invention is to provide apparatus, which is convenient and rapid to calibrate, for accurately determining the electrical characteristics of a superconductive material in a range of microwave frequencies and over a range of cryogenic temperatures.

Another object is to obtain, in such apparatus having a microwave cavity containing superconductive material at cryogenic temperatures, measurements of the microwave characteristics of the cavity unaffected by temperature and electrical conductivity effects in transmission elements to the cavity.

Another object is to provide such an apparatus wherein such cavities and materials may be conveniently interchanged.

Another object is to provide such an apparatus wherein heat conduction from such a cavity to the environment is minimized, thereby reducing errors due to temperature differences at the cavity and reducing the time for the cavity to cool before starting measurements.

A further object is to provide such apparatus adapted for convenient connection to closed cycle cryostatic cooling equipment and for use with existing microwave analysis techniques.

BRIEF DESCRIPTION OF THE DRAWINGS

Other objects, advantages and novel features of the invention will become apparent from the following detailed description when considered with the accompanying drawings wherein.

DESCRIPTION OF THE PREFERRED EMBODIMENT

Figure 1:
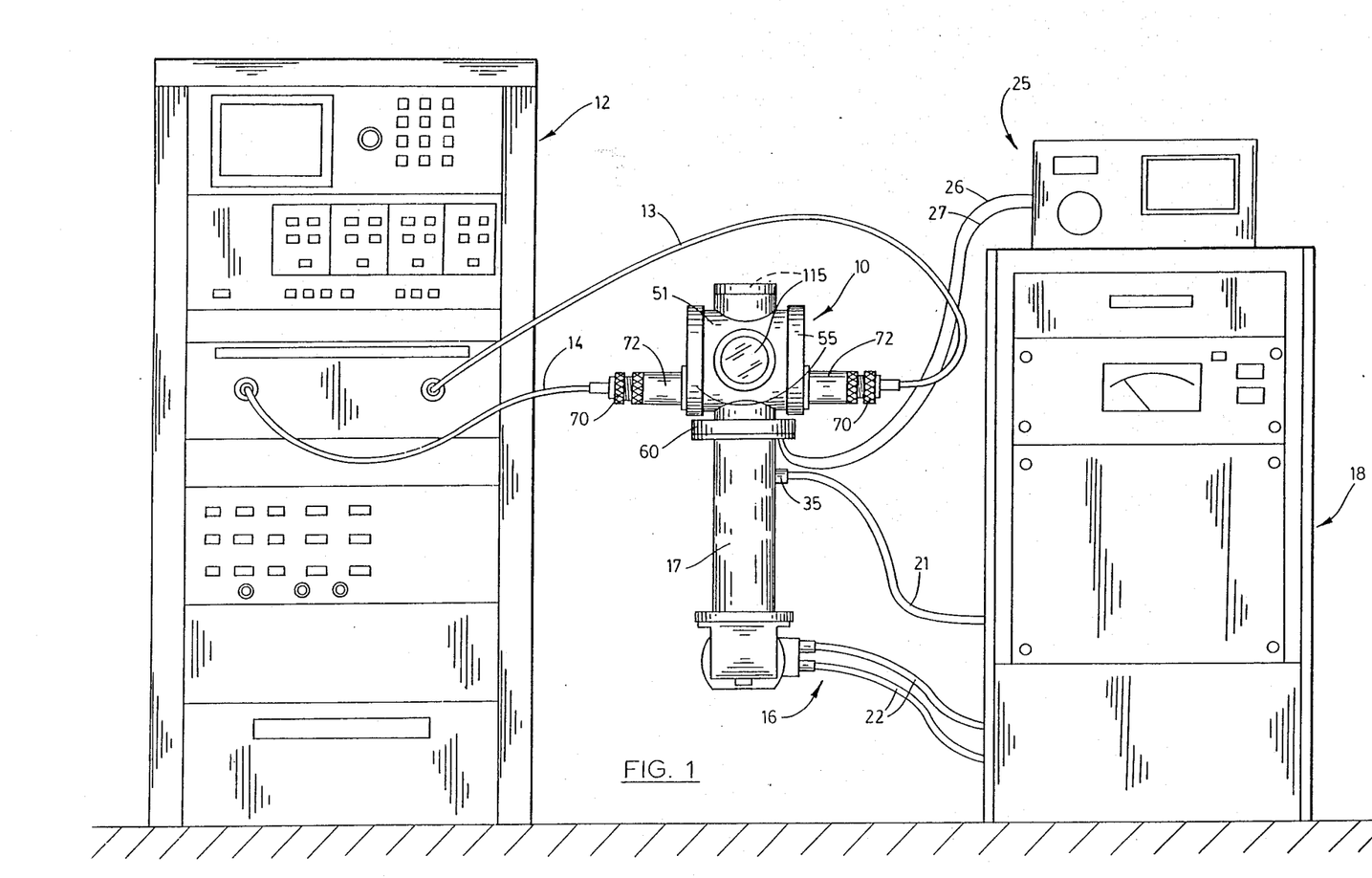
FIG. 1 is an elevation of apparatus, which embodies the principles of the present invention for determining the microwave characteristics of superconductive materials, in a representative operating environment with associated equipment.

FIG. 1 depicts apparatus 10 which embodies the principles of the present invention and is for use in testing to determine the electrical characteristics of superconducting material at microwave frequencies. Apparatus 10 is depicted with representative support equipment including a microwave network analyzer 12 which is connected to apparatus 10 by a pair of coaxial connectors 13 and 14. The support equipment also includes a combined vacuum and closed cycle cryostatic cooling system 16 which has a cold head 17 on which apparatus 10 is mounted in a manner subsequently described in detail. System 16 also has a machinery cabinet 18 connected to cold head 17 by a vacuum hose 21 and a pair of coolant hoses 22. Cold head 17 is mounted adjacent to analyzer 12 and cabinet 18 by any suitable elements, not shown. The support equipment further includes a temperature sensing and control system 25 electrically connected to apparatus 10 and head 17 by a temperature sensing connector 26 and by a heater power connector 27. It will be apparent to those skilled in the art that apparatus 10 may be used with a variety of well-known equipment corresponding to analyzer 12 and to systems 16 and 25. Therefore, such equipment will not be further described herein except as related functionally to apparatus 10.

Support system 16 includes elements shown in FIGS. 1-4 and has a cold finger 30. This finger is a rod terminating in screw-threads 31 and extended into apparatus 10 from cold head 17 which is fragmentarily represented in FIG. 3. The portion of finger 30 not shown in FIG. 3 extends into head 17 and is there cooled substantially to the liquification temperature of helium by helium circulated from cabinet 18 by hoses 22. The portion of finger 30 between screw threads 31 and the balance of head 17 is wound with an electric resistance winding 33 heated by power supplied by system 25 through connector 27 so that an element, which is subsequently described and is mounted on screw-threads 31, is brought to a selected temperature above such helium temperature by controlled heating determined by system 25 which senses the temperature of such element via a thermocouple or the like fixed to the element and providing a temperature signal to system 25 by connector 26. Cold head 17 has a vacuum connection, FIGS. 1 and 3, by which the cold head interior communicates through hose 22 with cabinet 18 of system 16. The cold head interior also communicates, in a manner subsequently described, with apparatus 10 so that system 16 is arranged to provide a vacuum within the apparatus for purposes of thermal insulation.

Analyzer 12 operates in a well-known manner to output microwave energy of selected frequencies by connectors 13 and 14 to a microwave circuit being tested. Analyzer 12 then receives this energy back through these connectors after transmission and reflection by the circuit for measurements by the analyzer of the power and phase relations of the returned energy. In order to separate effects due to the circuit from those due to transmission elements thereto and to leakage within the analyzer, the analyzer is calibrated with known transmission and reflection elements substituted for the circuit. For the most effective calibration the substitute elements must replace only the circuit of interest without any change in transmission elements to the circuit, a condition difficult to meet in practice since apparently minor variations in such things as curvature of a coaxial conductor or length of a wave guide due to temperature change are highly significant at microwave wavelengths.

The mathematics of such calibration, although involved, are well-known to those skilled in the art of microwave measurements and need only be discussed herein as related to specific substitute elements required for calibration and provided by apparatus 10. In general the calibration is utilized to generate "error boxes" which are mathematical expressions for circuits which may be inserted within and between connectors 13 and 14 to, in effect, cancel power and phase changes in the returned energy due to all causes except a circuit to be tested. The effects of these error boxes are then applied mathematically to the energy returned through connectors 13 and 14. In order to provide sufficient independent variables to generate the parameters of the error boxes required for calibration of an analyzer such as analyzer 12, it is usual to substitute successively for a circuit to be tested a through waveguide of one length between connectors 13 and 14, a through waveguide of another length between these connectors, and a pair of shorted waveguides individually terminating these connectors. It is apparent that the accuracy of calibration is increased if the calibration waveguides have dimensions corresponding to the dimensions of any waveguides substituted for.

Figure 2:
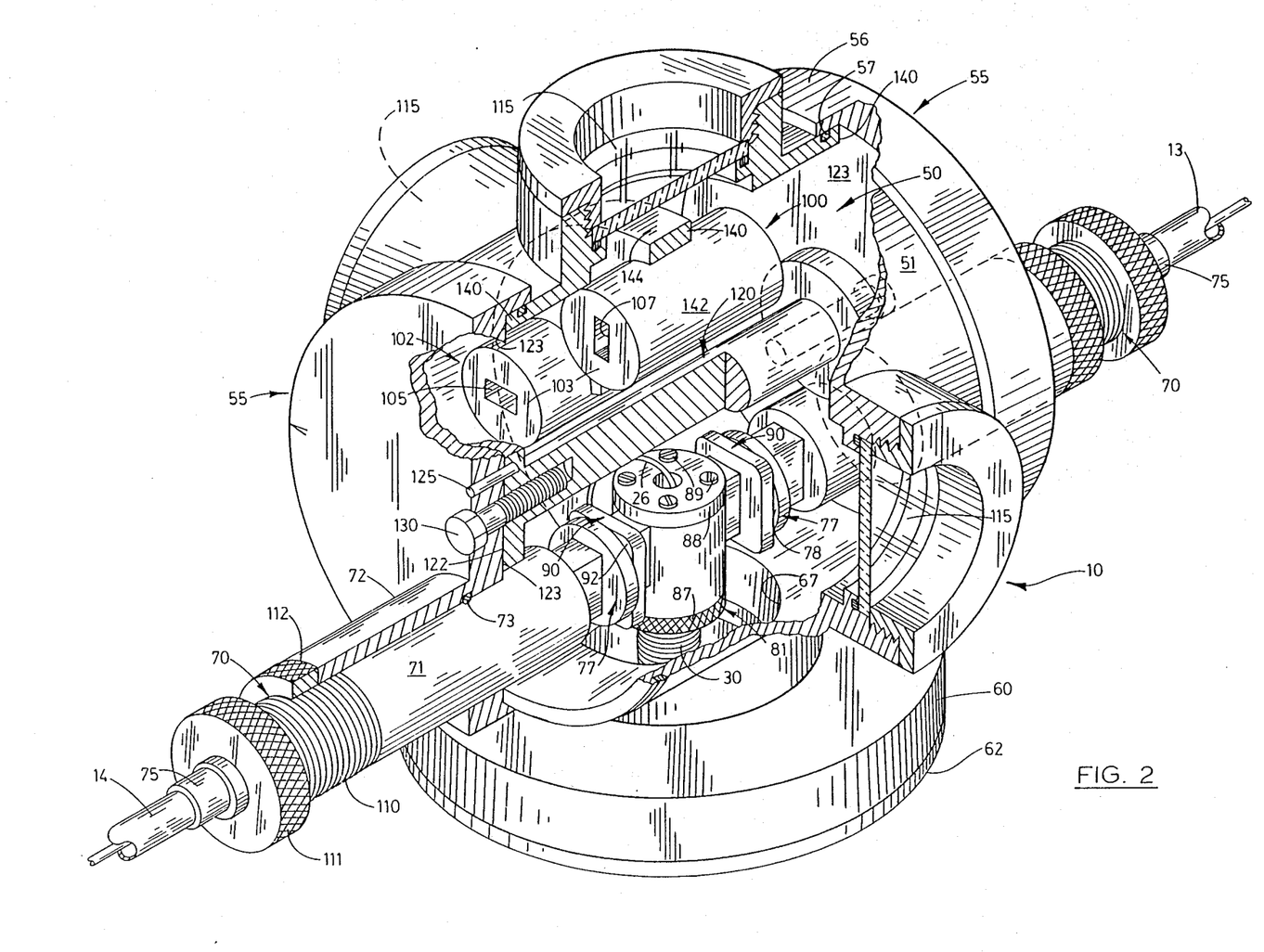
FIG. 2 is an isometric view of the apparatus of FIG. 1 with portions represented as partially broken away to show interior elements.
Figure 3:
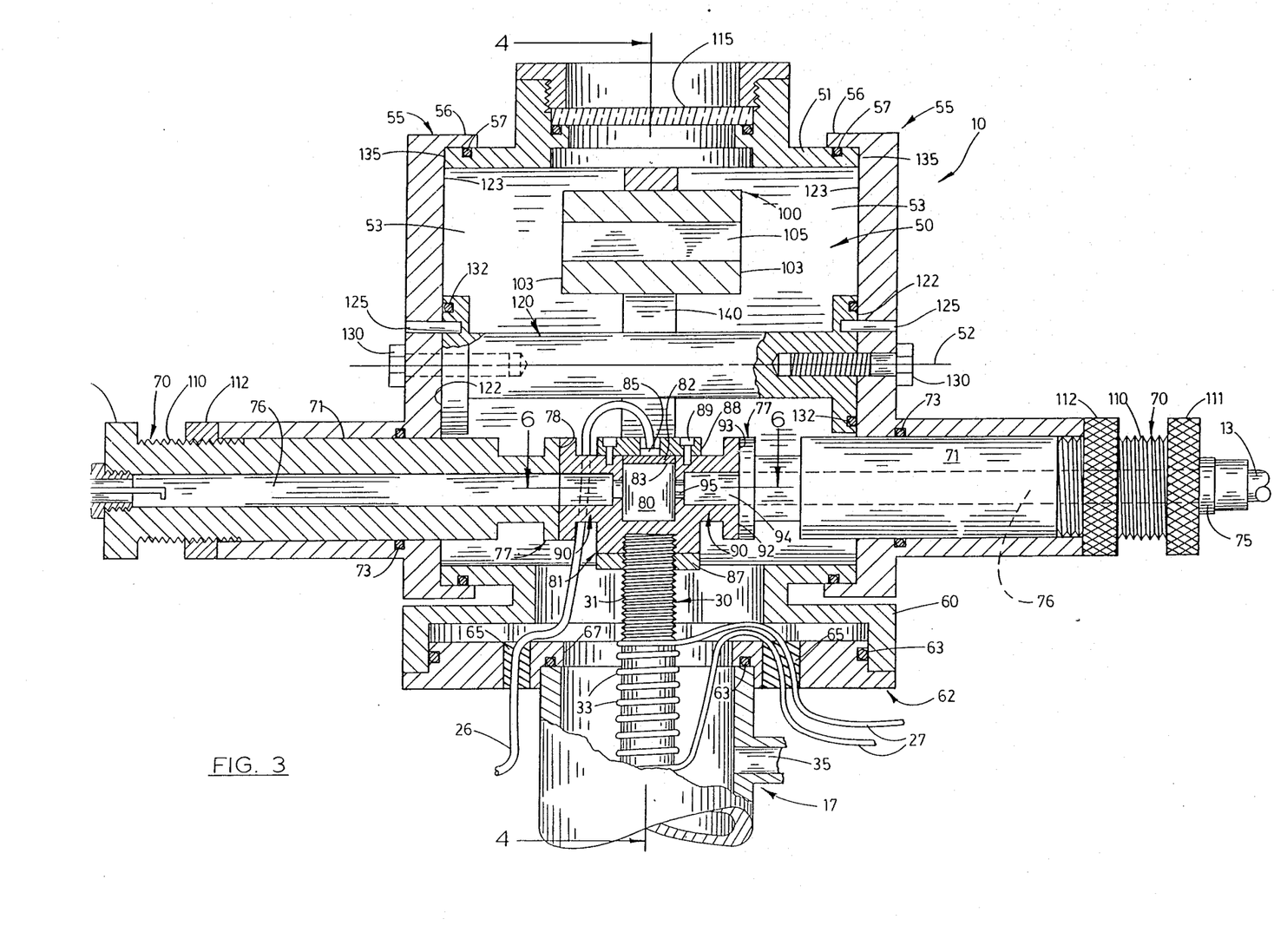
FIG. 3 is an axial section of the apparatus with an associated cold head which is fragmentarily represented, one connecting waveguide of the apparatus being depicted as axially sectioned and another such waveguide being depicted as unsectioned.
Figure 4:
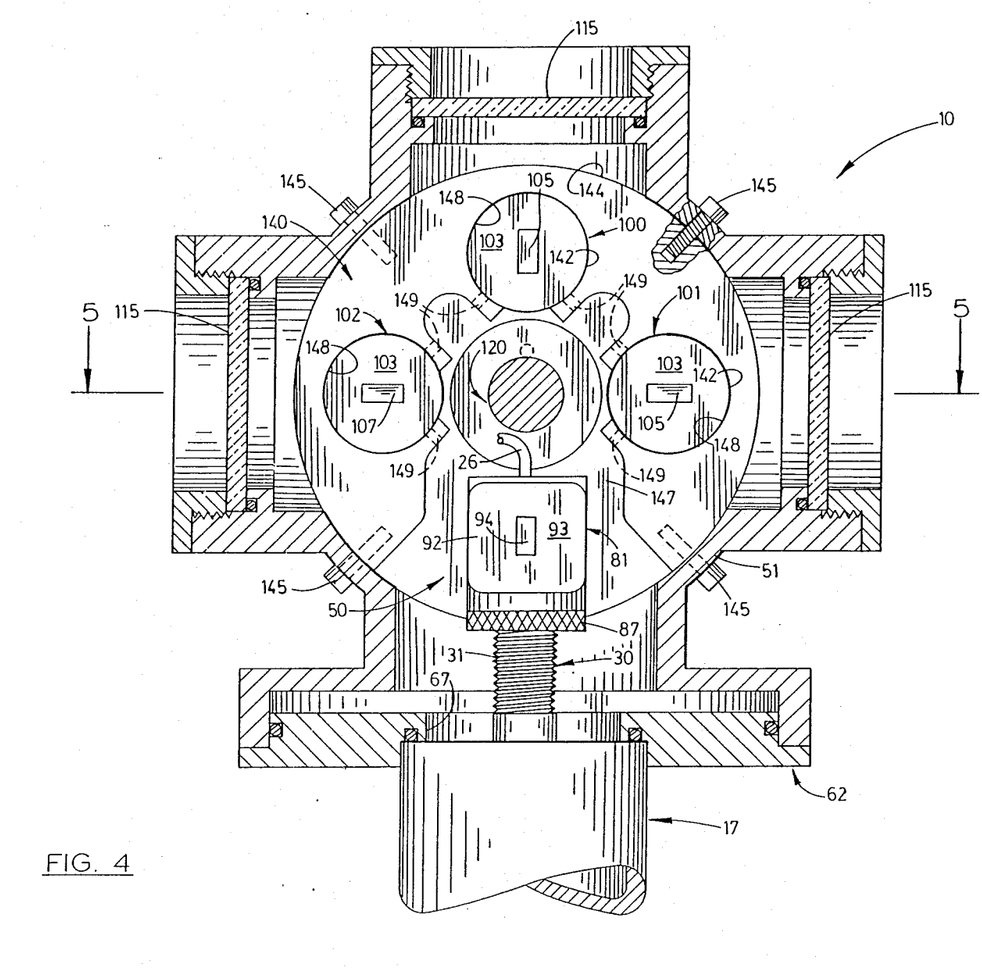
FIG. 4 is a diametrical section of the apparatus and cold head taken on line 4—4 of FIG. 3.

Referring now to FIGS. 2–4, it is seen that apparatus 10 has a cryogenic vacuum chamber 50 defined by a cylindrically tubular wall 51 having an axis 52 shown in FIG. 3. Wall 51 terminates axially and oppositely in a pair of circular openings 53 over which extend individually and in closing relation a pair of end plates or caps 55. Each cap 55 is cup-like and has a flange 56, identified in FIG. 3, conforming to and slidably fitted over the exterior of wall 51 so that the cap is mounted on the wall for pivotal movement relative thereto about axis 52. A pair of O-rings 57 are fitted in corresponding grooves circumscribing wall 51 individually within flanges 56 and serve as vacuum seals between the wall and caps during such movement and at other times.

Wall 51 has, at a side thereof depicted in the Figures as downwardly of chamber 50, a circular opening circumscribed by a flange 60 and receiving an adapter plate 62 by which the chamber is mounted on cold head 17. Plate 62, as best shown in FIG. 3, is detachably fixed in any suitable manner, as by screws not shown, to both wall 51 and head 17 so that finger 30 is substantially normal to axis 52 and disposed centrally between caps 55. A vacuum seal is provided for the plate to the wall and to the head by O-rings 63. The plate has a pair of openings for passage of connectors 26 and 27, these openings being vacuum sealed by any suitable plugs 65. Plate 62 has a central opening 67, identified in FIGS. 2–5, through which cold finger 30 extends centrally and from head 17 through wall 51 into chamber 50 in thermally insulated relation thereto since finger 30 does not contact wall 51 or plate 62. Opening 67 also provides vacuum communication between chamber 50 and vacuum connection 35 and, ultimately, cabinet 18.

Apparatus 10 has a pair of connecting waveguides 70, shown in FIGS. 1–3, and 5 and subsequently described in greater detail, these wave guides being sometimes referred to in the claims as "first wave guides". Each waveguide 70 has a cylindrical outer portion 71 which, axially, is parallel to axis 52 and spaced radially therefrom a predetermined distance substantially less than the inner radius of wall 51. Waveguide portions 71 extend individually and in pivotal and axially slidable relation through corresponding sleeves 72 fixed individually to caps 55. Each waveguide portion 71 is closely fitted within the corresponding sleeve 72, and an O-ring 73 is received in a groove therebetween so that the connecting waveguide 70 is fitted in vacuum sealed relation to the corresponding cap 55 which serves to mount the waveguide on wall 51 for pivotal movement relative thereto about axis 52. Each waveguide 70 has, as best shown in FIG. 3, an outer end provided with a well-known microwave connector 75 to a corresponding one of the coaxial connectors 13 or 14 of analyzer 12. The connector 75 serves to propagate microwave energy to and from the analyzer along a conventional waveguide passage 76 of rectangular cross section to an inner end of waveguide 70. This inner end terminates within wall 51 in a flange 77 which defines a connecting, separable waveguide or microwave junction, sometimes referred to in the claims as a "first flanged waveguide junction" or, for reasons subsequently apparent, as a "common separable waveguide junction". Flange 77 and the adjacent portion of waveguide 70 may be constructed from a conventional wave guide and flange, and flange 77 bears a planar face 78 or junction surface which is normal to axis 52 and thus extends transversely thereof.

As best shown in FIGS. 2 and 3, apparatus 10 has, for microwave energy provided by analyzer 12, a cylindrical resonant cavity 80 defined by a thermally conducting body 81 mounted on finger 30 in thermally conducting relation thereto. An element 82 of superconducting material for testing by apparatus 10 is mounted on body 81 in thermally conducting relation with the body and, therefore, finger 30. Element 82 is disposed in cavity 80 for impingement by and interaction with such microwave energy therein. This element may, as depicted in FIG. 3, be a disk mounted at one end of the cavity and bearing a end surface 83 of the cavity; however, such an element may have any other suitable configuration such as a helix extending axially within the cavity and formed from a wire-like portion of the superconductive material.

Body 81 has, at its end corresponding to element 82, any suitable temperature sensor 85 terminating connector 26 and thermally connected to this element so as to provide the temperature thereof to system 25. Body 81, preferably, has at the other end of cavity 80 screw-threads engageable with finger 30 by screw-threads 31 thereof, and this body is provided with a knurled lock collar 87 screw-threadably engaged with the finger. As a result of this arrangement, body 81 may be adjusted and secured into a desired position both rotationally about the axis of finger 30 and radially of axis 52. This arrangement also serves to secure the body in thermally conducting relation to finger 30 for conduction of heat from body 81 for cooling of element 82 to a predetermined temperature determined by system 25 in response to signal from sensor 85 and, typically, in a range of cryogenic temperatures including the transition temperature of a superconducting material from which element 82 is constructed. Body 81 has a cap 88 detachably mounted at one end of cavity 80 by screws 89 for convenient access to disk 82 of superconductive material and to sensor 85.

Body 81 has a pair of test or body waveguides 90 of equal length which extend in alignment and oppositely within chamber 50 from this body. Waveguides 90 are positioned, by use of the adjustment provided by screw-threads 31 and collar 87, so as to extend in a direction along axis 52 and to be spaced the same radial distance from this axis as waveguides 70. Each waveguide 90 terminates in a flange 92 which forms a test separable waveguide or microwave junction. Waveguide 90 and flange 92 conform to waveguide 70 and are similarly constructed and disposed with flange 92 bearing a planar face 93 or junction surface which is normal to axis 52 and thus extends transversely thereof. Referring to FIGS. 3, 4, 6, and 7, it is seen that each waveguide 90 has a passage 94 conforming to passage 76 of waveguide 70, opening through the corresponding face 93, and extending therefrom nearly to cavity 80 and to a point where passage 94 is closed by electrically conductive material of body 81 so that waveguide 90 is substantially shorted. However, body 81 defines a port 95 opening from passage 94 into cavity 80 for microwave energy to enter and leave the cavity.

Apparatus 10 has, as shown in FIGS. 2-5, a shorter through calibration waveguide 100, a longer through calibration waveguide 101, and a shorted calibration waveguide 102. Calibration waveguides 100-102 extend parallel to axis 52 and thus along this axis and waveguides 90. The calibration waveguides are spaced radially from axis 52 the same distance as waveguides 70 and 90, and each calibration waveguide has opposite ends terminating in a planar junction surface or face 103 which is normal to axis 52 and defines a calibration separable wave guide or microwave junction of the corresponding waveguide. The three calibration waveguides 100-102 are, together with the two aligned test waveguides 90, spaced equally and circumferentially about axis 52, as best seen in FIG. 4. These five wave guides are sometimes referred to collectively herein and in the claims as a "plurality of second waveguides" with the respective pair of junctions of each such second waveguide at its faces 93 or 103 being termed a "pair of second flanged waveguide junctions" and with the test waveguides being considered as a single waveguide having body 81 therein.

The length between faces 103 of through waveguide 100 and of shorted waveguide 102 is substantially equal to the distance between the faces 93 of body waveguides 90, while such length of longer through waveguide 101 is sufficiently greater than such distance for effective calibration in the manner previously noted. Each waveguide 100-102 is disposed so that its faces 103 are spaced oppositely and, preferably, substantially equally from finger 30 in a direction along axis 52.

Waveguides 100 and 101 each have a passage 105 conforming to passage 76 and extended through the waveguide between its faces 103. Waveguide 102 has a pair of passages 107 extending individually and inwardly of this waveguide from its faces 103 to a location 108 where passages 107 are shorted at a distance from such a face of waveguide 102 substantially equal to the distance between a face 93 of a test waveguide 90 and the associated port 95. As a result, calibration of apparatus 10 with waveguide 102 may cancel out the effects, including phase changes, of all transmission elements between ports 95 and analyzer 12, leaving for analysis only microwave resonance effects induced in cavity 80 by changes due to the temperature of element 82.

Referring to the above description and to FIGS. 2-6, it is apparent that chamber 50 and its wall 51 enclose body 81, test waveguides 90 thereof, and calibration waveguides 100-102 with junctions or faces 93 and 103 angularly spaced in relation to the axially corresponding one of the openings 55 and facing toward this one opening and the corresponding one of the connecting junctions or faces 78 of flange 77. Faces 78 are also within chamber 50 and face toward and faces 93 and 103 with waveguides 70 received in and extending through caps 55 so that the ends of these waveguides having coaxial connectors 75 are exterior to the chamber. It is evident that caps 55 are opposite of waveguides 90 and 100-102 in a direction along axis 52 with each face 93 or 103 adjacent to the corresponding cap and disposed so as to mate with the face 78 of the waveguide 70 of this cap. It can be seen that each cap 55 serves to mount the corresponding waveguide 70 on wall 51 for pivotal movement relative thereto to align, in a direction along axis 52, the waveguide face 78 with a selected one of the test waveguide faces 93 or calibration waveguide faces 103 and, by the slidable movement of the waveguide 70 in its sleeve 72, juxtaposition the face 73 with the selected face 93 or 103 and engage the juxtapositioned faces for transmission of microwave energy therebetween.

When a connecting waveguide 70 is so aligned with a selected one of the waveguides 90 or 100-102, the slidable mounting of connecting waveguide within its sleeve 72 results in ambient pressure externally of chamber 50 urging the connecting waveguide toward such selected wave guide and into firm engagement of the face 78 thereof with the aligned face 93 or 103. It has been found that this slidable mounting and use of ambient pressure effectively prevents the microwave leakage between such engaged faces which, typically, is only eliminated in similar waveguide connectors by the use of screwthreaded elements to draw flanges, such as flange 77, together. It is apparent that a plurality of such screw-threaded elements cannot be manipulated within a vacuum chamber and under vacuum without relatively complex mechanisms not required with apparatus 10.

Figure 5:
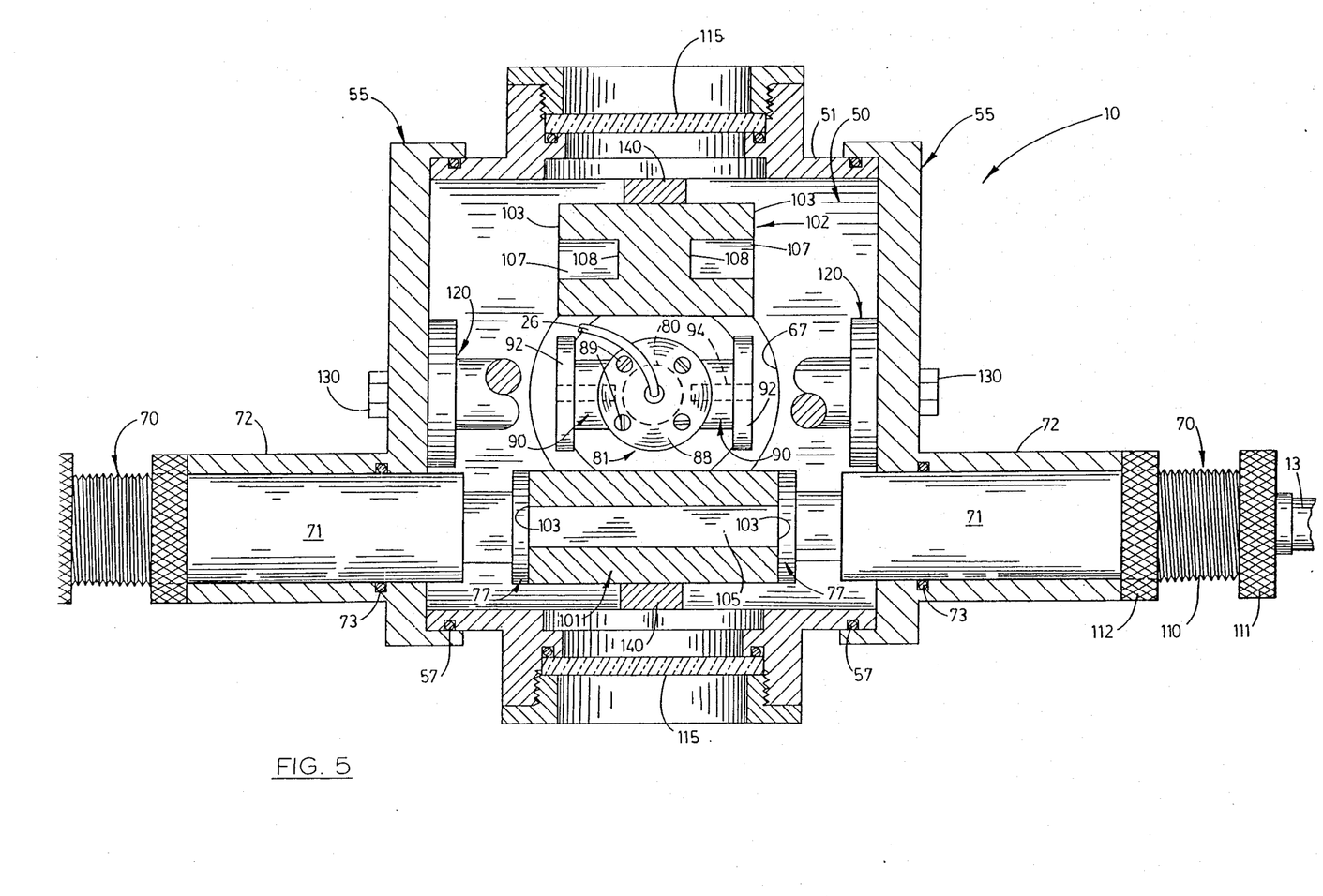
FIG. 5 is an axial section of the apparatus from the position of line 5—5 of FIG. 4 with portions of certain elements broken away and with the connecting waveguides in an alternate position.

To facilitate this use of ambient pressure to prevent microwave leakage, each waveguide 70, as shown in FIGS. 2, 3, and 5, has external screw-threads 110 outward of its cylindrical portion 71; terminates in a knurled knob 111 adjacent to connector 75; and bears a knurled ring 112 engaged with screw-threads 110. Ring 112 is utilized by engagement with sleeve 72 as a screw-jack to withdraw and hold connecting waveguide 70 from an aligned waveguide 90 or 100-102 while caps 55 are pivoted. It will be noted from FIG. 4 that passages 107 are oriented so that, if a passage 76 is aligned with its longer cross sectional dimension aligned with this dimension of one passage 107, pivoting of the corresponding cap 55 will result in substantial alignment of passage 76 with the other passages 107. Correction of any remaining misalignment is made possible by the pivotal mounting of each waveguide 70 in its sleeve 72 and is facilitated by knob 110 and ring 112.

In order to observe and correct any misalignment of waveguides 70 with waveguides 90 and 100–102 and to provide for any other need to view the interior of chamber 50 while under vacuum, wall 51 is provided, as shown in FIGS. 1–5, with three windows 115 which are of well-known and vacuum sealed construction and are spaced circumferentially about axis 52.

When using apparatus 10 for test or calibration, both first waveguides 70 must, typically, be aligned in a direction along axis 52 by pivotal movement of caps 55 with the same selected one of the second wave guides 90 or 100–102 so that both connectors 13 and 14 of analyzer 12 are connected to the same waveguide 100–102 or to cavity 80. To facilitate this alignment, apparatus 10 has an axle 120, best shown in FIGS. 2 and 3, extending along axis 52 and terminating oppositely in a pair of planar surfaces 122 individually engaged by planar inner sides 123 of caps 55. At each end of axle 120 a pin 125, which is spaced radially of axis 52, extends between and into a bore in the corresponding cap and a bore in the axle end, the bores being disposed so that waveguides 70 are aligned circumferentially about the axis. As a result, pivotal movement of either cap 55 to bring the face 73 of its first waveguide 70 into alignment with an adjacent face 93 or 103 of a selected second waveguide aligns such face of the other first waveguide 70 with the other such face of the selected waveguide.

Each cap 55 is detachably mounted on wall 51 and axle 120 by a capscrew 130 which extends along axis 52 and through a bore in the cap into screw-threaded engagement with the corresponding axle end so as to draw surfaces 122 and 123 firmly into engagement. To prevent vacuum leakage to chamber 50 around each capscrew 130, an O-ring 132 is disposed in circumscribing relation thereto between surfaces 122, and 123 as shown in FIG. 3. Removal of the capscrews 130 permits removal of caps 55 from wall 51 for complete access to chamber 50.

It is apparent that, because of temperature differences between the exterior and interior of chamber 50, there is differential expansion in a direction along axis 52 between wall 51 and axle 120 and that this expansion must be accommodated without vacuum leakage or without binding in the pivotal movement between caps 55 and wall 51. The wall has a pair of annular end surfaces 135 circumscribing axle 120 and individually adjacent to and conforming to cap surfaces 123 which face surfaces 135 and may be considered as having an annular region thereat. It is apparent that ambient pressure on caps 55 due to vacuum in chamber 50 urges each surface 123 toward the adjacent surface 135 and that, if these surfaces were engaged by the resulting force, friction between these surfaces would make pivotal movement between caps 55 and wall 51 difficult. Accordingly and so that the caps may pivot freely on the wall, surfaces 135 are spaced along axis 52 a first predetermined distance suitable for the purposes of chamber 50, and axle surfaces 122 are spaced along axis 52 a somewhat greater second predetermined distance, which is also substantially the distance between surfaces 123, to accommodate such thermal expansion and prevent engagement of surfaces 123 and 135 by vacuum forces. Caps 55 are positioned radially in relation to wall 51 by having the inner region of each flange 56 relatively closely, but pivotally, fitted relation to the adjacent region of wall 51 at O-ring 57. This O-ring provides any vacuum sealing required by such relation, and such regions are both at the exterior of chamber 50 and thus at substantially the same temperature so as to avoid binding due to thermal expansion.

As shown in FIGS. 2–5, apparatus 10 has a bulkhead 140 disposed centrally of chamber 50 and extending transversely thereof to support calibration waveguides 100–102 which have individual cylindrical external surfaces 142 parallel to axis 52. As best seen in FIGS. 2 and 4, the bulkhead has an exterior surface 144 conforming to the interior of wall 51 and fitted thereto at the portions thereof between windows 115 where the bulkhead is fixed in position, as by four screws 145 shown in FIG. 4. Bulkhead 140 has a cut away 147 to provide space for body 81 and elements associated therewith and has three arcuate notches 148 spaced angularly about axis 52. Each notch 148 conforms to a surface 144 and receives the corresponding one of the waveguides 100–102 so that faces 103 thereof are, in a direction along axis 52, adjacent to body waveguide faces 83. At each notch a pair of set screws 149 are screwthreadably mounted in bulkhead 140 for movement radially of the corresponding calibration waveguide to engage the waveguide and fix it in position in relation to chamber 50.

Figure 6:
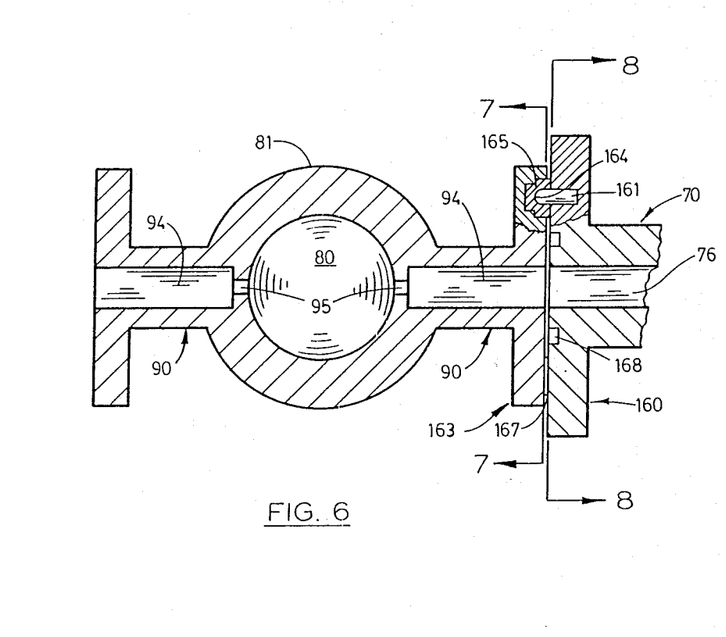
FIG. 6 is a section, at a scale enlarged from FIG. 3 and from the position of line 6—6 thereof, of a microwave cavity defining body of the apparatus with associated and aligned waveguides of alternative construction to those of FIG. 3.
Figure 7:
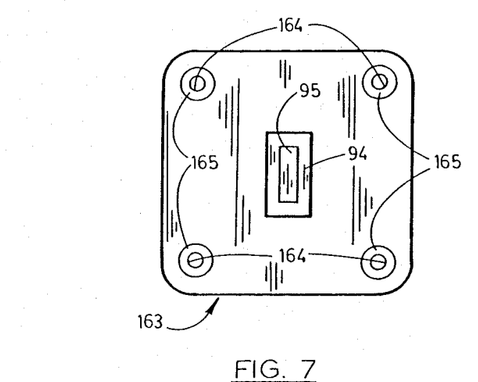
FIG. 7 is an elevation of a waveguide junction face from the position of line 7—7 of FIG. 6.
Figure 8:
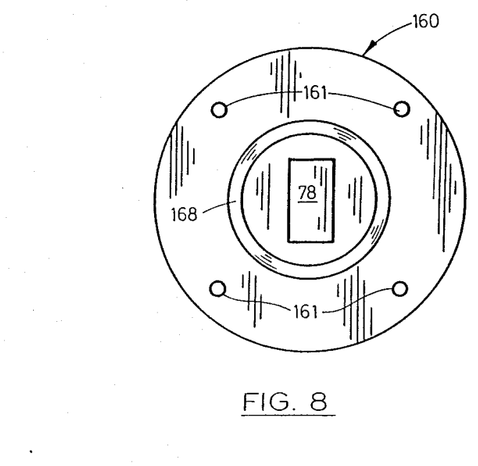
FIG. 8 is an elevation from the position of line 8—8 of FIG. 6 and showing a waveguide junction face mating with that of FIG. 7.

Leakage of microwave energy between each connecting waveguide 70 and a test waveguide 90 of body 81 is substantially prevented, as before stated, by flat engagement of the connecting waveguide face 78 with the test waveguide face 93 after juxtapositioning the waveguides by pivoting the corresponding cap 55 and then pivoting waveguide 70 so its passage 76 is aligned with the mating passage 94, such engagement being assisted by vacuum within chamber 50. An alternative waveguide junction configuration for avoiding such leakage and positively providing such alignment with greater thermal isolation between body 81 and the environment is shown in FIGS. 6–8 where waveguide 70 bears a flange 160 bearing four pins 161 spaced about passage 78 and extending axially therefrom toward waveguide 90 which bears a flange 163 having four sockets 164 configured and disposed to individually receive pins 161. Each socket 164 is formed in an insert 165 of any suitable thermal insulating material and has a depth such that, when the corresponding pin 161 is fully inserted in the socket, flanges 160 and 163 are separated by a predetermined gap 167. Since flanges 160 and 163 are not engaged and the only contact therebetween is by pins 161 which are of relatively small area and insulated by inserts 165, the conduction of heat is minimized to cryogenically cooled body 81 from waveguide 70 which extends into the environment from chamber 50 as seen in FIG. 3. Also, pins 161 preferably have rounded ends which tend to pivot waveguide 70 as it approaches waveguide so as to align passages 78 and 94. To prevent leakage of microwave energy through gap 167, flange 160 is a well-known choke flange having a groove 168 which circumscribes passage 74 at this gap and has a depth of about one-fourth the wavelength of such energy.

MODE OF OPERATION

The operation of apparatus 10 with associated systems 16 and for determination of the microwave properties of the superconductive material of disk 82 by interaction therewith of microwave energy in cavity 80 as measured by analyzer 12 and substantially without errors due to temperature variations in waveguide elements transmitting such energy between the analyzer and the cavity is believed readily apparent and will now be briefly described.

Apparatus 10 is initially set up with a body 81 of a desired configuration for a specific element 82 of superconductive material by removing end caps 55 from wall 51 and removing the wall from adapter plate 62 which may remain on cold head 17. Element 82 is inserted in cavity 80 and cap 88, with any suitable temperature sensor 85, is fixed to body 81 which is then fixed to finger 30 by screw-threads 31 and collar 87. Any suitable calibration waveguides 100-102 adapted to the waveguides 70 of body 81 may be installed in notches 148. It is apparent that apparatus 10 may be used with a variety of sensors, such as 85, and bodies, such as 81, adapted to various frequencies, temperatures, and elements 82, and that calibration waveguides of different lengths and of through or shorted configuration may be easily interchanged. Wall 51 then may then be installed on plate 62 and closed by caps 55, and system 16 started to provide a vacuum in chamber 50 and bring body 81 to a desired cryogenic temperature.

Finger 30 is substantially thermally isolated from wall 51, and thus the environment, by the construction of cold head 17 and such a vacuum in chamber 50, while calibration waveguides 100-102 are thermally connected to wall 51 only by bulkhead 140 and are thermally isolated from body 81 by such vacuum. It has been found that an effective vacuum for this purpose is obtained upon cooling body 81 to the cryogenic temperatures of interest after reducing the pressure within chamber 50 to an absolute pressure of about 50 microns of mercury with system 16, since such cooling then freezes residual gases in the chamber. As a result, body 81 with superconductive element 82 can be brought rapidly to a desired cryogenic temperature and this temperature varied without substantial change in the lengths of waveguides 70 and 100-102 which are relatively short so that the effects of any changes are minimal.

After establishing the necessary vacuum in chamber 50 and when the temperature of body 81, and thus superconductive element 82, has stabilized as controlled and indicated by system 25, apparatus 10 is calibrated with analyzer 12 by pivoting caps 55 about axis 52 to align waveguides 70 successively with calibration waveguides 100-102 and, at each calibration waveguide, transmitting microwave energy from the analyzer to the waveguide to obtain calibration data as previously described. Caps 55 are then pivoted to align waveguides 70 with test waveguides 90. During these operations, axial movements of waveguides 70 to accommodate differences in the overall lengths of waveguides 90 and 100-102 are made by sliding waveguides axially in sleeves 72, the sliding movements in cap 55 and pivotal movements thereof being made without loss of vacuum in chamber 50 and without substantial change in the temperature of element 82. Microwave energy is then transmitted from analyzer 12 to cavity 80 through one or both of the microwave junctions, which are formed between waveguide 70 and waveguide 90 where their respective faces 78 and 93 are aligned and are engaged by ambient pressure outside chamber 50, while changing the temperature of element 82 with system 25 and measuring changes in the microwave resonance of cavity 80 as affected by changes in the microwave properties of this element corresponding to temperature changes of the superconducting element 82.

Obviously, many modifications and Variations of the present invention are possible in light of the above teachings. It is, therefore, to be understood that within the scope of the following claims the invention may be practiced otherwise than as specifically described.

We claim:

1. Apparatus for determining microwave characteristics of a superconductive material having a transition temperature, the apparatus comprising:
   an element constructed of said superconductive material;
   a body defining a resonant cavity for microwave energy and having means for mounting said element at said cavity for impingement by said energy;
   a test waveguide extending from said body and terminating in a test waveguide junction;
   a calibration waveguide extending along said test waveguide and terminating in a calibration waveguide junction;
   a wall defining a vacuum chamber enclosing said body, said test waveguide, and said calibration waveguide;
   a cold finger extending from said body through said wall to conduct heat from said body and maintain said element at a temperature in a range of temperatures including said transition temperature;
   a connecting waveguide terminating at one end in a connecting microwave junction and having an opposite end connectable to microwave analyzer equipment; and
   means for mounting said connecting waveguide on said wall with vacuum sealed movement relative to said wall so as to juxtaposition said connecting junction to one junction selected from said test junction and said calibration junction without loss of vacuum in said chamber and without substantial change in said temperature of said element.

2. The apparatus of claim 1 wherein:
   said wall defines a circular opening into said chamber;
   said test junction and said calibration junction face said opening and are angularly spaced in relation thereto;
   said mounting means comprises a plate extending over said opening and mounted on said wall so that said relative movement is pivotal; and
   said connecting waveguide is received in said plate with said connecting junction facing said test junction and said calibration junction, so that, by such pivotal movement, said connecting junction is selectively alignable with said test junction and said calibration junction.

3. The apparatus of claim 1 wherein said test junction and said calibration junction are disposed within said chamber in facing relation to said mounting means, and said mounting means receives said connecting wave guide:

with said connecting junction disposed within said chamber and facing toward said test junction and said calibration junction;

with the connecting wave guide extending from the connecting junction through said mounting means so that said opposite end is disposed exteriorly of said chamber; and for slidable movement of said connecting waveguide through said mounting means toward and from said test junction and said calibration junction, so that ambient pressure externally of said vacuum chamber urges said connecting wave guide toward such one junction and into microwave energy transmitting relation therewith.

4. Test apparatus comprising:

a microwave network analyzer having a pair of connectors, said analyzer providing and receiving microwave energy at said connectors for analysis of a microwave circuit connected thereto;

cryogenic vacuum chamber support equipment including a vacuum system, a cold finger, a cooler for bringing said finger to a predetermined range of cryogenic temperatures, and a control system for maintaining an element which is thermally connected to said finger at a predetermined temperature in said range;

a thermally conducting body mounted on said finger, said body defining a resonant cavity for such microwave energy;

a pair of test waveguides mounted on said body for transmitting such energy to and from said cavity, said test waveguides extending oppositely from said body along a predetermined axis and at a predetermined radial distance therefrom, and each of said test waveguides terminating in a junction surface extended transversely of said axis;

a plurality of calibration waveguides extending along said axis at said radial distance therefrom, each of said calibration waveguides terminating oppositely in a pair of junction surfaces extended transversely of said axis;

a wall circumscribing said axis so as to define a vacuum chamber containing said body, said test waveguides, and said calibration waveguides;

means for connecting said vacuum system in vacuum providing relation to said chamber;

means for mounting said wall on said cooler with said finger extending through said wall to said body and with said finger in substantially thermally isolated relation to said wall;

a pair of caps disposed oppositely, in a direction along said axis, of said test wave guides and of said calibration waveguides;

means for mounting said caps on said wall with vacuum sealed relation thereto and with pivotal movement of said caps about said axis relative to said wall;

a pair of connecting waveguides extending individually through said caps along said axis and at said radial distance therefrom, each connecting waveguide terminating within said wall at a junction surface extended transversely of said axis and disposed for alignment by said pivotal movement about said axis to a selected junction surface of said calibration waveguides and said test waveguides; and means for mounting each of said connecting waveguides in vacuum sealed relation on the corresponding one of said caps for slidable movement relative thereto in a direction along said axis to juxtaposition the junction surface of the connecting waveguide to such a selected junction surface.

5. The apparatus of claim 4 further comprising a superconductive element having a transition temperature and mounted on said body in thermally connected relation to said finger for cooling of said element to a temperature in such a temperature range which includes said transition temperature, said element being disposed at said cavity for electromagnetic interaction with such microwave energy resonant therein for analysis of such interaction by said analyzer.

6. A test device comprising:

a cryogenic vacuum chamber including a tubular wall having an axis and a pair of opposite and open ends and including a pair of caps individually closing said ends, each cap being mounted on the corresponding end for pivotal and vacuum sealed movement about said axis relative to said wall;

a pair of first waveguides individual to said caps, each first waveguide extending through the corresponding cap and being fitted thereto for vacuum sealed movement in a direction along said axis relative to said cap and each first waveguide terminating inwardly of said wall in a first flanged waveguide junction disposed in radially spaced relation to said axis; and a plurality of second waveguides mounted on and interiorly of said wall and extended along said axis, each second waveguide terminating oppositely in a pair of second flanged waveguide junctions individually adjacent to said caps, each of said second junctions mating with the corresponding one of said first junctions and being disposed in corresponding radially spaced relation about said axis, so that alignment of each first junction with a selected one of said second junctions is obtainable by such pivotal movement of the one of said caps corresponding to the first junction and so that, subsequent to said alignment, the first junction and the second junction are, by such movement along said axis of the one of the first waveguides corresponding to the first junction, engageable for transmission of microwave energy between the first junction and the second junction.

7. The device of claim 6 wherein:

each pair of said second junctions corresponding to each of said second waveguides is aligned circumferentially of said axis;

the device further comprises an axle extending between said caps and connecting said caps for such pivotal movement together; and said caps are disposed on said axle so that said first junctions are aligned circumferentially of said axis, so that such pivotal movement of one of said caps about said axis aligns both of said first junctions with a pair of said second junctions corresponding to a selected one of said second waveguides.

8. The device of claim 7 wherein there is differential expansion along said axis between said wall and said axle and wherein:

said wall has a pair of first annular surfaces individual to said caps and circumscribing said axle, said first surfaces being spaced therealong a predetermined distance;

each of said caps has a second annular surface conforming to and facing the corresponding first annular surface;

said caps are mounted on said axle with said second surfaces spaced a distance greater than said predetermined distance and said differential expansion so that said caps pivot freely on said wall despite said differential expansion; and said device further comprises a pair of vacuum sealing rings individual to said ends and disposed between each thereof and the corresponding one of said caps.

9. The device of claim 6 further comprising:

a thermally conductive body disposed in one of said second waveguides and defining a resonant cavity for such microwave energy transmitted between one of said second junctions of the second waveguide and one of said first junctions aligned with the second junction;

an element mounted on said body in thermally conducting relation thereto and disposed in said cavity so that resonance of said energy therein is affected by changes in the properties of said element corresponding to temperature changes thereof; and means extended from said body and through said wall in thermally insulated relation thereto for conducting heat from said body to induce such temperature changes in said element.

10. The device of claim 9 wherein the device is for use with an analyzer for microwave energy and the device further comprises microwave connector means disposed on each of said first waveguides outwardly of the corresponding cap from said chamber for connection of such an analyzer to the first waveguide.

11. In apparatus for determining electrical characteristics of a superconductive material at a microwave frequency and having:

a body defining a resonant cavity for microwave energy, mounting an element which is constructed of such material and which bears a surface of said cavity, and defining a port for such energy to enter and leave said cavity;

cryogenic equipment thermally connected to said element for maintaining said element at a predetermined cryogenic temperature;

a microwave analyzer providing said energy and measuring variations in microwave resonant characteristics; and waveguide elements for transmitting such energy between said cavity and said analyzer, said waveguide elements having variations in microwave transmission characteristics caused by temperature variations of said elements;

an improvement for calibrating such apparatus to measure microwave characteristics of said cavity without substantial errors due to such variations in such transmission characteristics, wherein the improvement comprises:

said waveguide elements including a body waveguide extended from said port and terminating adjacent thereto at a test separable waveguide junction;

a calibration waveguide terminating at a calibration separable waveguide junction;

a connecting waveguide having a connection for said analyzer and having a termination at a common separable waveguide junction;

means for supporting said body waveguide and said calibration waveguide with said test junction disposed adjacent to said calibration junction; and means for supporting said connecting waveguide with movement between said test junction and said calibration junction so as to juxtaposition said common junction selectively and in microwave transmitting relation to said test junction and said calibration junction, for calibration of said analyzer as connected to said waveguide elements when said common junction is juxtapositioned to said calibration junction and for measurement of such resonant characteristics of said cavity as affected by said material when said common junction is juxtapositioned to said test junction.

12. The apparatus of claim 11 wherein said cryogenic equipment includes a vacuum system and a cold finger on which said body is mounted in thermally connected relation and wherein said improvement further comprises:

wall means, through which said finger extends in thermally insulated relation, for defining a vacuum chamber enclosing said body; and means for connecting said system to said chamber to maintain a vacuum therein so as to thermally isolate said body from the environment of the apparatus.

13. The apparatus of claim 12 wherein said wall means defines said chamber so that the chamber encloses said body waveguide and said calibration waveguide in thermally isolated relation from said environment.

* * * * *